United States Patent [19]

Young et al.

[11] Patent Number: 5,004,743
[45] Date of Patent: Apr. 2, 1991

[54] PYRIDYL STYRENE DIALKANOIC ACIDS AS ANTI-LEUKOTRIENE AGENTS

[75] Inventors: Robert N. Young, Senneville; Robert Zamboni, Longueuil; Jacques Y. Gauthier, Laval, all of Canada

[73] Assignee: Merck Frosst Canada, Inc., Kirkland, Canada

[21] Appl. No.: 125,637

[22] Filed: Nov. 25, 1987

[51] Int. Cl.$^5$ ............... C07D 211/72; C07D 211/70; C07D 211/68; C07D 279/10
[52] U.S. Cl. ............... 514/227.8; 546/294; 546/291; 546/276; 546/284; 546/261; 546/262; 546/263; 546/331; 546/335; 546/337; 546/341; 546/281; 546/194; 546/278; 546/273; 514/357; 514/346; 514/347; 514/351; 514/332; 514/340; 514/343; 514/318; 514/235.5; 514/252; 514/343; 514/13; 514/14; 514/15; 514/16; 514/17; 514/18; 514/19; 544/131; 544/124; 544/58.6; 544/60; 544/360; 544/364; 544/365
[58] Field of Search ............... 546/294, 291, 276, 284, 546/261, 262, 263, 331, 335, 337, 341, 342; 514/357, 346, 347, 351, 332, 340, 227.8, 12–19

[56] References Cited

U.S. PATENT DOCUMENTS 4,629,497 12/1986 Nickell et al. .................. 546/294

FOREIGN PATENT DOCUMENTS 219436 4/1987 European Pat. Off. ............ 546/294
228959 7/1987 European Pat. Off. ............ 546/294

Primary Examiner—Mary C. Lee
Assistant Examiner—Robert C. Whittenbaugh
Attorney, Agent, or Firm—Gabriel Lopez; Hesna J. Pfeiffer

[57] ABSTRACT

Compounds having the formula:

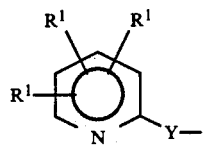

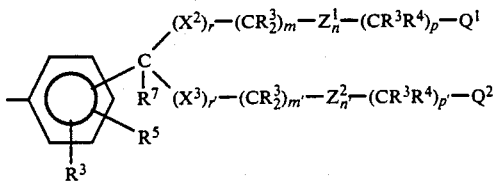

are leukotriene antagonists and inhibitors of leukotriene biosynthesis. These compounds are useful as anti-asthmatic, anti-allergic, anti-inflammatory, and cytoprotective agents.

10 Claims, No Drawings

PYRIDYL STYRENE DIALKANOIC ACIDS AS ANTI-LEUKOTRIENE AGENTS

BACKGROUND OF THE INVENTION

The leukotrienes and their biological activities, especially their roles in various disease states and conditions have been described. For example, see U.S. Pat. No. 4,683,325 (July 28, 1987), which is incorporated herein by reference.

Several classes of compounds exhibit ability to antagonize the action of leukotrienes in mammals, especially humans. See for example: UK 2,058,785 and 2,094,301; and EP 56,172, 61,800 and 68,739.

EP 110,405 (June 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

The present invention relates to compounds having activity as leukotriene and SRS-A antagonists or inhibitors of the biosynthesis of the leukotrienes, to methods for their preparation, to intermediates useful in their preparation and to methods and pharmaceutical formulations for using these compounds in mammals (especially humans).

Because of their activity as leukotriene antagonists or biosynthetic inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or myocardial tissue; liver parenchymal damage caused by hepatoxic agents such as CCl$_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

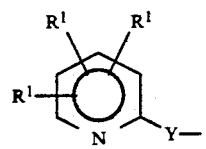

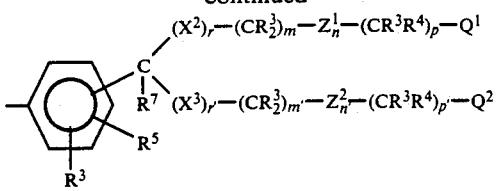

wherein:

$R^1$ is H, halogen, $C_1$–$C_{18}$ alkyl, $C_2$–$C_8$ alkenyl, $C_2$–$C_8$ alkynyl, —CF$_3$, —SR$^2$, —S(O)R$^2$, —S(O)$_2$R$^2$, —NR$^3$R$^3$, —OR$^3$, —COOR$^3$, (C=O)R$^3$, —C(OH)R$^3$R$^3$, —CN, —NO$_2$, —N$_3$, substituted or unsubstituted phenyl, substituted or unsubstituted benzyl, substituted or unsubstituted 2-phenethyl, or substituted or unsubstituted pyridyl;

$R^2$ is $C_1$–$C_8$ alkyl, $C_2$–$C_8$ alkenyl, $C_2$–$C_8$ alkynyl, —CF$_3$, substituted or unsubstituted phenyl, substituted or unsubstituted benzyl, or substituted or unsubstituted 2-phenethyl;

$R^3$ is H or $R^2$;

$R^4$ is H, halogen, —NO$_2$, —CN, —OR$^3$, —SR$^3$, NR$^3$R$^3$, or $C_1$–$C_8$ alkyl;

$CR^3R^4$ may be the radical of a naturally occurring amino acid;

$R^5$ is halogen, —NO$_2$, —N$_3$, —CN, —SR$^2$, —NR$^3$R$^3$, —OR$^3$, $C_1$–$C_8$ alkyl, or —(C=O)R$^3$;

$R^6$ is —(CH$_2$)$_s$—C(R$^7$R$^7$)—(CH$_2$)$_s$—R$^8$ or —CH$_2$CONR$^{12}$R$^{12}$;

$R^7$ is H or $C_1$–$C_4$ alkyl;

$R^8$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical W—R$^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is —SR$^{11}$, —OR$^{12}$, or —NR$^{12}$R$^{12}$;

$R^{11}$ is $C_1$–$C_6$ alkyl, —(C=O)R$^{14}$, unsubstituted phenyl, or unsubstituted benzyl;

$R^{12}$ is H, $R^{11}$, or two $R^{12}$ groups joined to the same N may form a ring of 5 or 6 members containing up to two heteroatoms chosen from O, S or N;

$R^{13}$ is $C_1$–$C_8$ alkyl, $C_2$–$C_8$ alkenyl, $C_2$–$C_8$ alkynyl, —CF$_3$, or unsubstituted phenyl, benzyl, or 2-phenethyl;

$R^{14}$ is H or $R^{13}$;

$R^{15}$ is $R^3$ or halogen;

$R^{16}$ is H, $C_1$–$C_4$ alkyl, or OH;

m and m' are independently 0–8;

n and n' are independently 0 or 1;

p and p' are independently 0–8;

m+n+p is 1–10 when $X^2$ is O, S, S(O), or S(O)$_2$;

m+n+p is 0–10 when $X^2$ is CR$^3$R$^{16}$;

m'+n'+p' is 1–10 when $X^3$ is O, S, S(O), or S(O)$_2$;

m'+n'+p' is 0–10 when $X^3$ is CR$^3$R$^{16}$;

r is 0 or 1 when $Z^1$ is HET (—R$^3$, —R$^5$);

r is 1 when $Z^1$ is —CONR$^3$;

r' is 0 or 1 when $Z^2$ is HET(—R$^3$, —R$^5$);

r' is 1 when $Z^2$ is CONR$^3$;

s is 0–3;

$Q^1$ and $Q^2$ are independently —COOR$^3$, tetrazole, —COOR$^6$, —CONHS(O)$_2$R$^{13}$, —CN, —CONR$^{12}$R$^{12}$, —CHO, —CH$_2$OH, —COCH$_2$OH, —NHS(O)$_2$R$^{13}$; or if $Q^1$ or $Q^2$ is COOH and $R^4$ is —OH, —SH, or —NHR$^3$ then Q$^1$ or Q$^2$ and R$^4$ and the carbons through which they are attached may form a heterocyclic ring by loss of water;

W is O, S, or NR$^3$;

X$^1$ is O, S, —S(O)—, —S(O)$_2$—, —NR$^3$, or —CR$^3$R$^3$—;

X$^2$ and X$^3$ are independently O, S, S(O), S(O)$_2$, or CR$^3$R$^{16}$;

Y is —CR$^3$=CR$^3$—, —C≡C—, —CR$^3$R$^3$—X$^1$—, —X$^1$—CR$^3$R$^3$—, —CR$^3$R$^3$—X$^1$—CR$^3$R$^3$—,

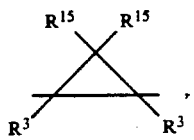

C=O,

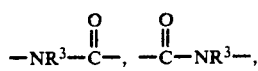

O, S, or NR$^3$;

Z$^1$ Z$^2$ independently —CONR$^3$— or —HET(—R$^3$, —R$^5$)—;

HET is

and the pharmaceutically acceptable salts thereof.

Alkyl, alkenyl, and alkynyl are intended to include linear, branched, and cyclic structures and combinations thereof.

As used herein, the term "alkyl" includes "loweralkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-ethyl-2,2-methyl-4-propylnonyl, cyclododecyl, adamantyl, and the like.

As used herein, the term "loweralkyl" includes those alkyl groups of from 1 to 7 carbon atoms. Examples of loweralkyl groups include methyl, ethyl, propyl, isopropyl, butyl, sec and tert butyl, pentyl, hexyl, heptyl, cyclopropyl, cyclobutyl, cyclo pentyl, cyclohexyl, cycloheptyl, 2-methylcyclopropyl, cyclopropylmethyl, and the like.

Alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

As used herein, the term "alkoxy" includes those alkoxy groups of from 1 to 3 carbon atoms of either a straight, branched, or cyclic configuration. Examples of alkoxy groups include methoxy, ethoxy, propoxy, isopropoxy, cyclopropyloxy, and the like.

Substituted phenyl, benzyl, 2-phenethyl and pyridyl include 1 or 2 substituents on the aromatic ring selected from C$_1$-C$_6$ alkyl, R$^{10}$, NO$_2$, halogen, —COR$^7$, —COR$^{10}$, SCF$_3$, CN, and CF$_3$.

Halogen includes F, Cl, Br and I.

The prodrug esters of Q (i.e., when Q=—COOR$^6$) are intended to include the esters such as are described by Saari et al., J. Med. Chem., 21, No. 8, 746-753 (1978), Sakamoto et al., Chem. Pharm. Bull., 32, No. 6, 2241-2242 (1984) and Bundgaard et al., J. Med. Chem., 30, No. 3, 451-454 (1987).

When Q and R$^4$ and the carbons through which they are attached form a ring, the rings thus formed include lactones, lactams, and thiolactones.

It is intended that the definitions of any substituent (e.g., R$^1$, R$^2$, m, Q, X, etc.) in a particular molecule be independent of its definitions elsewhere in the molecule. Thus, —NR$^3$R$^3$ represents —NHH, —NHCH$_3$, —NHC$_6$H$_5$, etc.

The heterocycles formed when two groups join through N include pyrrolidine, piperidine, morpholine, thiamorpholine, piperazine, and N-methylpiperazine.

The naturally occurring amino acids, the radicals of which may be CR$^3$R$^4$, include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z qeometric isomers.

Preferred compounds of Formula I are those wherein:

R$^1$ is H, halogen, C$_1$-C$_8$ alkyl, C$_2$-C$_8$ alkenyl, C$_2$-C$_8$ alkynyl, —CF$_3$, —SR$^2$, —S(O)R$^2$, —S(O)$_2$R$^2$, —NR$^3$R$^3$, —OR$^3$, —CN, substituted or unsubstituted phenyl, substituted or unsubstituted benzyl, substituted or unsubstituted 2-phenethyl, or substituted or unsubstituted pyridyl;

R$^2$ is C$_1$-C$_8$ alkyl or —CF$_3$;

R$^3$ is H or R$^2$;

R$^4$ is H, —OR$^3$, —SR$^3$, NR$^3$R$^3$, or C$_1$-C$_8$ alkyl;

CR$^3$R$^4$ may be the radical of a naturally occurring amino acid;

R$^5$ is H, halogen, —CN, —SR$^2$, —OR$^3$, C$_1$-C$_8$ alkyl, or —(C=O)R$^3$;

R$^6$ is —(CH$_2$)$_s$—C(R$^7$R$^7$)—(CH$_2$)$_s$—R$^8$ or —CH$_2$CONR$^{12}$R$^{12}$;

R$^7$ is H or C$_1$-C$_4$ alkyl;

R$^8$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical W—R$^9$;

R$^9$ contains up to 21 carbon atoms and is (1) a hydrocarbon radical or (2) an acyl radical of an organic acyclic or monocyclic carboxylic acid containing not more than 1 heteroatom in the ring;

R$^{10}$ is —SR$^{11}$, —OR$^{12}$, or —NR$^{12}$R$^{12}$;

R$^{11}$ is C$_1$-C$_6$ alkyl, —(C=O)R$^{14}$, unsubstituted phenyl, or unsubstituted benzyl;

R$^{12}$ is H, R$^{11}$, or two R$^{12}$ groups joined to the same N may form a ring of 5 or 6 members containing up to two heteroatoms chosen from O, S or N;

R$^{13}$ is C$_1$-C$_8$ alkyl, —CF$_3$, or unsubstituted phenyl, benzyl, or 2-phenethyl;

R$^{14}$ is H or R$^{13}$;

R$^{15}$ is R$^3$ or halogen;

R$^{16}$ is H, C$_1$-C$_4$ alkyl, or OH;

m and m' are independently 0–4;
n and n' are independently 0 or 1;
p and p' are independently 0–4;
m +n +p is 1–10 when $X^2$ is O or S;
m +n +p is 0–10 when $X^2$ is $CR^3R^{16}$;
m'+n'+p' is 1–10 when $X^3$ is O or S;
m'+n'+p' is 0–10 when $X^3$ is $CR^3R^{16}$;
r is 0 or 1 when $Z^1$ is HET (—$R^3$, —$R^5$);
r is 1 when $Z^1$ is $CONR^3$;
r' is 1 when $Z^1$ is HET(—$R^3$, $R^5$);
r' is 0 or 1 when $Z^2$ is $CONR^3$;
s is 0–3;
$Q^1$ and $Q^2$ are independently —$COOR^3$, tetrazole, —$COOR^6$, —$CONHS(O)_2R^{13}$, —$CONR^{12}R^{12}$, —NH-S(O)$_2R^{13}$; or if $Q^1$ or $Q^2$ is COOH and $R^4$ is —OH, —SH, or —$NHR^3$ then $Q^1$ or $Q^2$ and $R^4$ and the carbons through which they are attached may form a heterocyclic ring by loss of water;
W is O, S, or NH;
$X^1$ is O, S, —$NR^3$, or —$CR^3R^3$—;
$X^2$ and $X^3$ are independently O, S, or $CR^3R^{16}$;
Y is —$CR^3$=$CR^3$—, —C≡C—, —$CR^3R^3$—$X^1$—, or —$X^1$—$CR^3R^3$—;
$Z^1$ and $Z^2$ are independently —$CONR^3$— or —HET-(—$R^3$, $R^5$) ; HET is

and the pharmaceutically acceptable salts thereof.

It will be understood that in the discussion of methods of treatment which follows, references to the compounds of Formula I are meant to also include the pharmaceutically acceptable salts and the lactone, lactam, and thiolactone forms.

The compounds of Formula I are active as antagonists of SRS-A and especially of leukotriene $D_4$. These compounds also have modest inhibitory activity on leukotriene biosynthesis but are primarily of therapeutic interest as antagonists. The activity of the compounds of Formula I can be detected and evaluated by methods known in the art. See for example, Kadin, U.S. Pat. No. 4,296,129.

The ability of the compounds of Formula I to antagonize the effects of the leukotrienes and to inhibit the biosynthesis of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. They are also effective in the treatment of inflammatory diseases of the eye.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in U.S. Pat. No. 4,683,325 (July 28, 1987).

The leukotriene antagonist properties of compounds of the present invention were evaluated using the following assays.

Guinea-Pig Ileum Preparation for Evaluation of Antagonists of Leukotriene $D_4$ and Other Mediators Tissue:

Sections of ileum were taken from male Hartley strain guinea pigs (Charles River, U.S.A.) 300 to 500 g which were sacrificed by a blow to the head and exsanguinated. Terminal ileum was removed, cleaned with warm Tyrode's solution and then divided into segments of approximately 1.5-2.0 cm each. The segments of ileum were then mounted under 1 g tension in a 20 ml organ bath containing 10 ml of Tyrode's solution with the following composition (mM): NaCl, 137; KCl, 2.7; $MgSO_4.7H_2O$, 0.8; $CaCl_2$, 1.8; $NaH_2PO_4$, 0.42; $NaHCO_3$, 11.9; Dextrose, 5.6. The bathing solution was continuously aerated with 95% $O_2$ and 5% $CO_2$ and bath temperature was maintained at 37° C. The beta-adrenoceptor blocker, timolol (0.5 μg/ml) and the antimuscarinic agent atropine (1.0 μM) were present in the Tyrode's solution. Isometric tension changes were recorded using Grass FT03 force displacement transducers (Grass Instrument G., Quincy, Mass.) connected to a Beckman Type R Dynograph. The output (analog) signals from all channels of the Beckman Dynograph were converted to digital signals (DL-12 Data Logger, Buxco Electronics). These signals were subsequently fed into an IBM-XT computer for storage and subsequent analysis (Buxco Electronics Custom Software). In order to wash tissue, the bath solution was automatically aspirated and replaced with a constant volume (10 ml) of fresh solution by means of timer controlled solenoid valves.

Antagonist Testing:

After the tissues were stable a standard dose of 0.3 ng/ml $LTD_4$ (100 μl) was repeatedly added (timer controlled Harvard Pump) to the bath every 4.5 minutes (1 minute contact, 30 second wash, 3 minute rest) until a consistent response was obtained (minimum of 4 responses). Addition of $LTD_4$ was performed automatically with two 4 channel Harvard Apparatus Syringe Pumps which delivered 100 μl (final bath concentration 0.3 ng/ml) of agonist simultaneously to all tissues every 4.5 minutes. Following each addition of $LTD_4$ the tissue was washed with Tyrode's solution until baseline tension was re-established. After consistent responses were obtained the tissues were used to screen compounds.

Usually, 10 μl of a 10 mg/ml solution of the compound to be tested was added to the bath 30 seconds prior to the addition of $LTD_4$. The compound and $LTD_4$ remained in contact with the tissue until the maximum tension was developed (1 minute) after which the tissue was washed repeatedly until the baseline was re-established. Percent inhibition relative to the immediately preceding control response was computed on an IBM-XT for each dose of test compound (Buxco Electronics Custom Software). If the compound was active (greater than 50% inhibition) then tests were performed with 10 fold serial dilutions until inhibition was less than 50%. Provided the response was inhibited by less than 20%, the tissue was used immediately to evaluate another compound. When the response was inhibited by greater than 20%, cycles of LTD$_4$ alone were added until a consistent response was re-established.

In order to determine the specificity of the active compounds, they were tested against contractions induced by a standard dose of histamine (50 ng/ml) using a similar protocol to that described above (1/2 minute contact time, 30 seconds wash and 2 minutes rest).

LTD$_4$ Binding:

The results for LTD$_4$ binding were determined by the method of S. S. Pong and R. N. DeHaven, Proc. Nat. Acad. Sci. USA, 80, 7415–7419 (1983).

Compounds of Formula I were tested using the following assay to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15–24 hr. the rats are sacrificed (CO$_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered, through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for LTB$_4$ content by adding an aliquot to a second 500 μl portion of the PMN at 37° C. The LTB$_4$ produced in the first incubation causes aggregation of the second PMN, which is measured as a change in light transmission. The size of the assay aliquot is chosen to give a submaximal transmission change (usually −70%) for the untreated control. The percentage inhibition of LTB$_4$ formation is calculated from the ratio of transmission change in the sample to the transmission change in the compound-free control.

The following assays can be used to evaluate compounds which are either leukotriene antagonists or inhibitors of leukotriene biosynthesis or which possess a combination of these two properties.

Antigen Challenge 'in vitro' Assay

Male guinea pigs weighing 300–350 g are sensitized by injecting (intraperitoneally) 0.5 ml of a suspension containing 0.4 mg of egg albumin (Ovalbumin, Grade V, Sigma Chemical Co.) and 4.0 g of aluminum hydroxide in 19.6 ml of saline. Two weeks are permitted for sensitization to occur.

Three sensitized quinea pigs are stunned and exsanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No.7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% O$_2$ and 5% CO$_2$ at 37° C. Mepyramine ($7 \times 10^{-6}$ M), atropine ($1 \times 10^{-7}$ M), and indomethacin ($1.4 \times 10^{-6}$ M) are added to the buffer to block the response to released histamine, acetylcholine, and cyclooxygenase products. To record responses, one end of the tracheal chain is attached to a Gould Statham UC-2 force displacement transducer which is connected to a Beckman Type R Dynograph. The preparations are allowed to equilibrate for one hour during which time the tissues are automatically washed (10 ml volume displacement) every 6 minutes.

[1] modified Krebs solution in grams/liter and (mM): NaCl—6.87 (120); glucose—2.1 (11); NaHCO$_3$—2.1 (25); KCl—0.32 (4.72); CaCl$_{2-0.28}$ (2.5); MgSO$_4$.7H$_2$O—0.11 (0.5); KH$_2$PO$_{0.16}$ (1.2); pH at bathing solution =7.35±0.05.

After the equilibration period the tissues are primed with methacholine (10 μg/ml) washed and allowed to recover to baseline. The tissues are treated again with a second dose of methacholine, washed, allowed to return to baseline and washed for an additional hour.

Two chains are used as a control. These are incubated in a concentration of egg albumin (0.1 μg/ml) sufficient to induce an average contraction of 50–80% of the methacholine response.

Each compound to be tested is added (at a final bath concentration of 10 μg/ml) 20 minutes prior to challenging the tissue with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methylsergide bimaleate is supplied by Sandoz Ltd., Basel.

The challenge and subsequent respiratory recordings are carried out in a clear plastic box with internal dimensions $10 \times 6 \times 4$ inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 30 μg/kg methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intraveneously 2 minutes prior to challenge. They are either dissolved in saline or 1% methanol or suspended in 1% methocel. The volume injected is 1 ml/kg (intravenously) or 10 ml/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, antiallergic or anti-inflammatory use and generally, uses other than ecytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co administration of a compound of the Formula I with a non-steroidal anti-inflammatory drug (NSAID) that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts derived from inorganic bases include aluminum, ammonium, calcium, copper, ferric, ferrous, lithium, magnesium, manganic, manganous, potassium, sodium, zinc salts and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylamino ethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzene sulfonic, benzoic, camphorsulfonic, citric, ethane sulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p toluenesulfonic acid and the like. Particularly preferred are hydrobromic, hydrochloric, phosphoric, and sulfuric acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well known in the art of pharmacy.

Dosage forms include tablets, troches, dispersions, suspensions, solutions, capsules, creams, ointments, aerosols, and the like.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cyto-protective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001–1% by weight solutions or suspensions of the compounds of Formula I in an acceptable ophthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five qroups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof. NSAIDs which are within the scope of this invention are those disclosed in U.S. Pat. No. 4,683,325 (July 28,1987).

Pharmaceutical compositions comprising the Formula I compounds may also contain inhibitors of the biosynthesis of the leukotrienes such as are disclosed in U.S. Pat. No. 4,666,907 (Apr. 19, 1987), U.S. Pat. No. 4,663,307 May 5, 1987), U.S. Pat. No. 4,611,056 (Sept. 9, 1986), and U.S. Pat. No. 4,634,766 (Jan. 6, 1987), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP 56,172 (July 21, 1982) and U.S. Pat. No. 4,424,231 (Jan. 3, 1984); and in U.K. Patent Specification No. 2,058,785, which are hereby incorporated herein by reference.

Pharmaceutical compositions comprising the Formula I compounds may also contain as the second active ingredient prostaglandin including thromboxane antagonists such as those disclosed in U.S. Pat. No. 4,536,507 (Aug. 20, 1985), U.S. Pat. No. 4,237,160 (Dec. 2, 1980), EP 166,591 (Jan. 2, 1986), and EP 234,708 (Sept. 2, 1987). They may also contain histidine decarboxylase inhibitors such as α-fluoromethyl histidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in *Nature*, vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK 2,038,821 (e.g., UK-37248 and dazoxiben hydrochloride), U.S. Pat. No. 4,217,357 (e.g., UK-34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK-38485), or EP 98,690 (e.g., CV 4151).

The combination compositions can be administered orally or other than orally; e.q., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed above.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following compounds (formula I') are within the scope of the invention:

TABLE 1

| EX | $R^1$ | $R^1$ | Y | $R^3$ | A | B |
|---|---|---|---|---|---|---|
| 1 | H | 5-Ph | CH=CH | H | $SCH_2CH_2CO_2H$ | $SCH_2CH_2CO_2H$ |
| 2 | H | 6-Ph | CH=CH | H | $SCH_2CH_2CO_2H$ | $SCH_2CH_2CO_2H$ |
| 3 | 6-Br | 5-Ph | CH=CH | H | $SCH_2CH_2CO_2H$ | 3-($CO_2H$)-Phe |
| 4 | 4-S(O)$_2$CH$_3$ | 5-(4(SCF$_3$)Phe) | CH$_2$CH$_2$ | 5-Ph | $SCH_2CH_2CO_2H$ | 3-($CO_2H$)-Phe |
| 5 | H | 5-(4(C$_2$H$_5$)Phe) | C≡C | H | $SCH_2CH_2CO_2H$ | 3-($CO_2H$)-6-($COCH_3$)Phe |
| 6 | 6-Ph | 3-S(O)$_2$CH$_3$ | CH=CH | H | $SCH_2CH_2CO_2H$ | 3-($CO_2H$)-Phe |
| 7 | 6-Ph | H | CH$_2$O | 4-CH$_3$ | $SCH_2CH_2CO_2H$ | 3-($CO_2H$)-Phe |
| 8 | 5(2-(CF$_3$)Phe) | H | CH$_2$O | H | $SCH_2CH_2CO_2H$ | 3-($CO_2H$)-Phe |
| 9 | 6-Ph | 5-CF$_3$ | CH$_2$CH$_2$ | H | $SCH_2CH_2CO_2H$ | 3-($CO_2H$)-Phe |
| 10 | 5-Cl | 6-Ph | C≡C | H | $SCH_2CH_2CO_2H$ | 3-($CO_2H$)-Phe |
| 11 | 5-Ph | 6-COCH$_3$ | CH=CH | H | $SCH_2CH_2CO_2H$ | $CH_2CH_2$-(2($CO_2H$)Phe) |
| 12 | 6(6-Cl-2-Pyr) | H | CH=CH | H | $SCH_2CH_2CO_2H$ | $SCH_2CH_2CO_2H$ |
| 13 | 5-(4-Cl-Phe) | H | CH=CH | 6-CF$_3$ | $SCH_2CH_2CO_2H$ | $SCH_2CH_2CO_2H$ | where Ph = phenyl; Pyr = ![pyridyl]; and Phe = ![phenyl]

Compounds of the present invention can be prepared according to the following methods. Temperatures are in degrees Celsius.

METHOD A

Pyridine derivative II is treated with aldehyde IIa in the presence of a suitable catalyst like $ZnCl_2$ at temperatures greater than 120° or by heating with a dehydrating agent, most preferably by heating with acetic anhydride to give adduct III. Bromo acid derivative IV is treated first with 2 equivalents of base such as BuLi in a suitable solvent such as THF at −100° then at −78° with III to afford alcohol V. Alcohol V is reacted with thiol VI in the presence of a suitable catalyst such as $BF_3$ or $AlCl_3$ to give adduct VII.

METHOD B

Alternatively, adduct V can be transformed to VIII, where W is a suitable leaving group such as Cl, using reaction conditions such as $CCl_4$/trioctylphosphine. VIII is reacted with thiol VI in the presence of a suitable base such as $K_2CO_3$ to give adduct VII.

METHOD C

Referring to Method C, a pyridine derivative of structure IX is prepared by standard methods from pyridine derivatives of formula II using N-chloro- or N-bromosuccinimide. IX is then reacted with a compound of formula X in the presence of a suitable base such as NaOH, NaH, $K_2CO_3$ or NaOMe in an inert solvent such as THF with warming if necessary to provide the adduct XI. Using the reactions described in Methods A or B, adduct XI is transformed to XII.

METHOD D

Referring to Method D, bromo derivative XIII can be treated with $PPh_3$ in a suitable solvent such as toluene or $CH_3CN$ with warming if necessary to provide phosphonium salt XIV. The phosphonium salt XIV is treated with n-butyllithium then with lactol XV to afford styrene adduct XVI. Alcohol XVI is transformed to ester XVII using conventional methods such as $CrO_3$/pyridine followed by $MnO_2$/NaCN/AcOH/MeOH. Styrene adduct XVII is condensed with thiol VI in the presence of a suitable catalyst such as $AlCl_3$ to give thiol ether XVIII.

When A=CN, XVIII is reduced with a reagent such as $SnCl_2$/HCl to give aldehyde XIX. Pyridine derivative IX is treated with $PPh_3$ in a suitable solvent such as toluene to give phosphonium salt XX. The phosphonium salt XX is treated with n-butyl lithium then with XIX to give styryl quinoline XXI.

When A=OMe, XVIII is demethylated using a suitable reagent such as $BBr_3$ to qive phenol derivative XXII. Phenol XXII is condensed with pyridine derivative IX using a suitable catalyst such as $K_2CO_3$ to afford adduct XXIII.

METHOD E

Referring to Method E, pyridine derivative II is first treated with LDA and then with bromo derivative XXIV to afford adduct XXV. Cyano derivative XXV is reduced to aldehyde XXVI with a reagent such as $SnCl_2$/HCl. Using the methodology described in Method A or B, XXVI is converted to XXVII.

METHOD F

Reaction of styryl-aldehyde III with an alkanoic acid or tetrazole substituted with a thiol or hydroxy group in an inert solvent such as benzene in the presence of a suitable catalyst such as $BF_3$.OEt affords the styrylpyridine derivative XXVIII. Compound XXVIII is representative of the structure I compounds.

METHOD G

Reaction of adduct Xl with an alkanoic acid or tetrazole substituted with a thiol or hydroxy group in an inert solvent such as benzene in the presence of a suitable catalyst such as $BF_3$.OEt affords the pyridine derivative XXIX.

Generally, the qroups $Q^1$ and $Q^2$ may be modified by hydrolysis of an ester group, removal of a blocking group, or conversion of a nitrile to an amide or tetrazole by heating with tributyltin azide, thus providing additional examples of the leukotriene antagonists of the present invention.

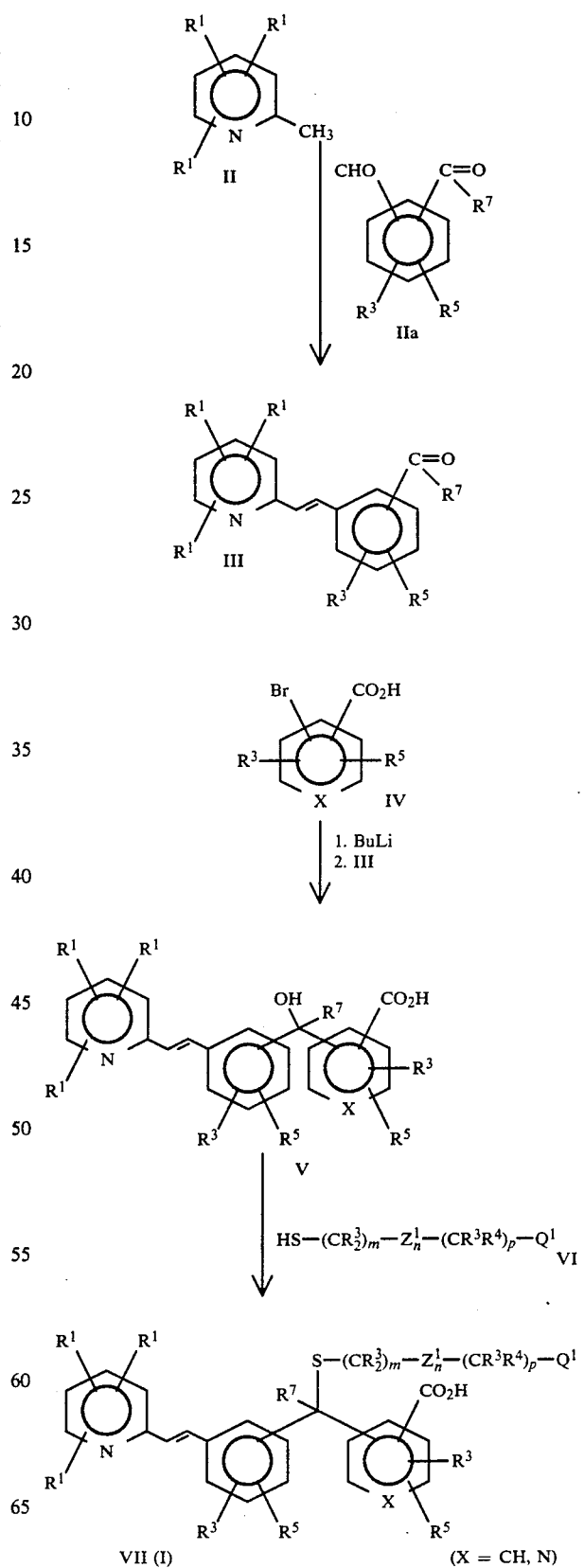

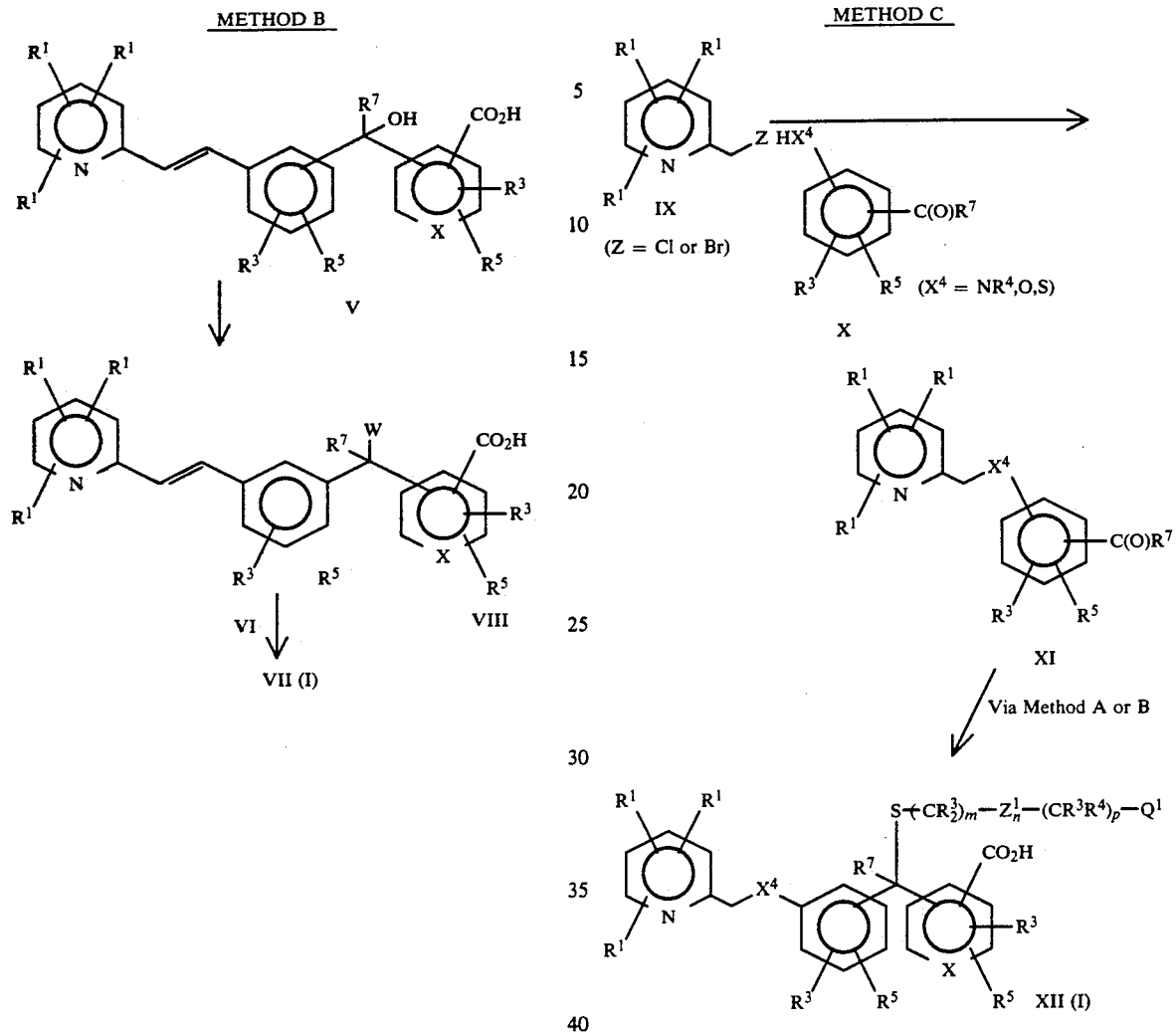

METHOD D
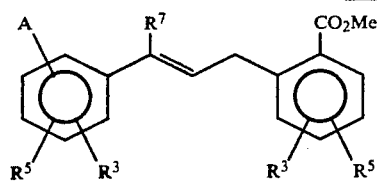
XVII
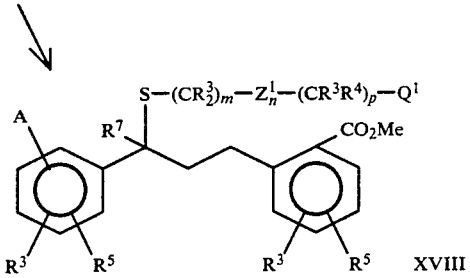
XVIII
XVIII (A = CN)
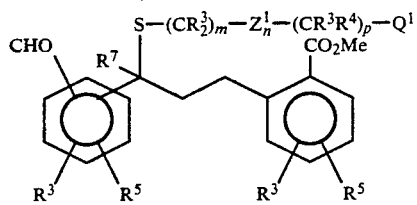
XIX
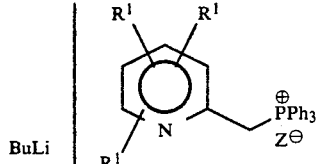 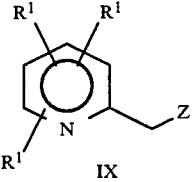
XX    IX
BuLi
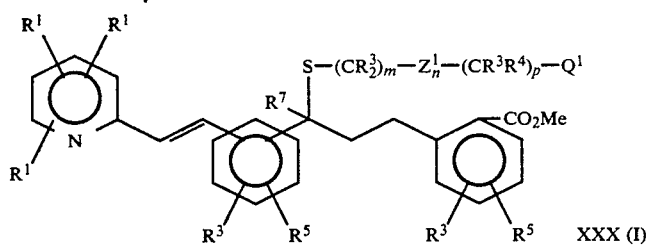
XXX (I)
XVIII (A = OMe)
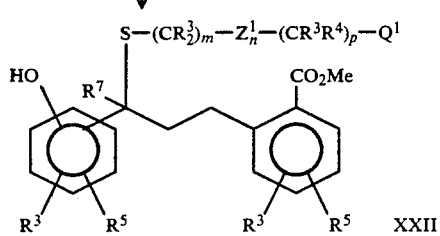
XXII
IX

METHOD D
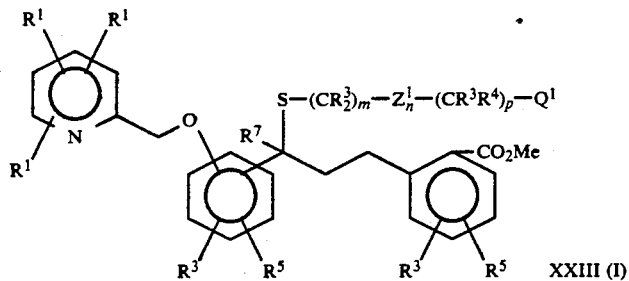
METHOD E
II $\xrightarrow{\text{1. LDA}}_{\text{2.}}$ 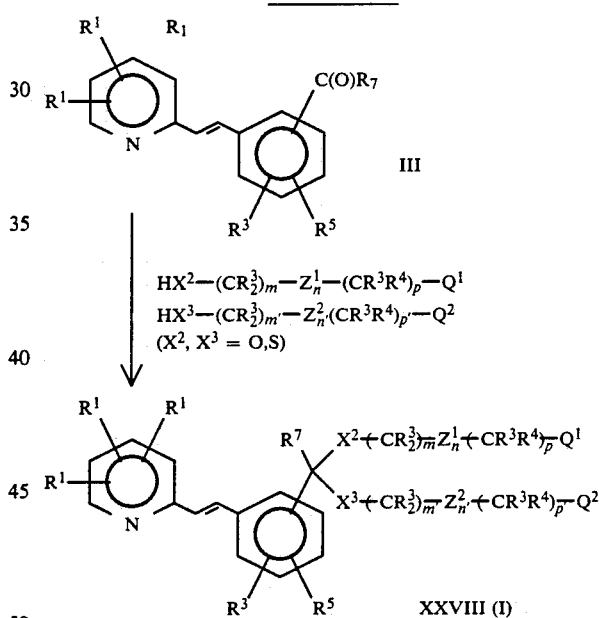
METHOD F
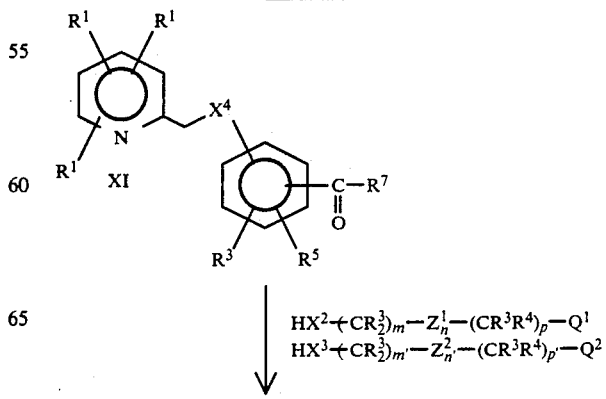
METHOD G

-continued
METHOD G

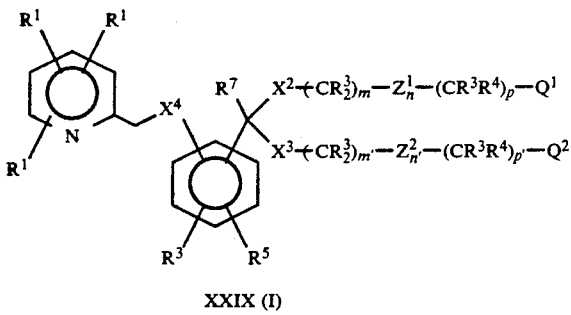

XXIX (I)

The invention is further defined by reference to the following examples, which are intended to be illustrative and not limiting.

All temperatures are in decrees Celsius.

EXAMPLE 1

Preparation of 5-(3-(2-(6-phenylpyridin-2-yl)ethenyl)phenyl)-4,6-dithianonanedioic acid, disodium salt Step 1 Preparation of 5-benzoyl-2-pentanone To a $-10°$ C. solution of 4-acetylbutyric acid (1 mm, 130 mg) in benzene (1.5 cc) and dichloromethane (1.5 cc) was added oxalyl chloride (1.1 mm, 140 mg) followed by a drop of N,N-dimethylformamide; the mixture was then brought to 25° C. for 30 minutes. It was then cooled to $-10°$ C. and AlCl$_3$ (2 mm, 266 mg) was added portion wise and the mixture held at 0° C. for 1 hour. Ice was added, followed by 1N HCl. Then the product was extracted with ethyl acetate (2×10 cc). The organic phase was washed with dilute NaHCO$_3$/brine and the solvents removed in vacuo to afford the title compound.

p.m.r. (CD$_3$COCD$_3$) δ 7.3–8.1 (m, 5H), 2.9–3.1 (t, 2H), 2.4–2.7 (t, 2H), 1.9–2.2 (m, 5H).

Step 2 Preparation of 2-methyl-6-phenylpyridine

To a refluxing mixture of hydroxylamine.HCl (2.1 g) in acetic acid (5 cc) was added a solution of 5-benzoyl-2-pentanone (1.9 g) (step 1) in acetic acid (5 cc) and the suspension refluxed for 3 hours. Acetic acid was then removed in vacuo, the residue treated with H$_2$O (25 cc) and extracted with ethyl acetate (3×25 cc); the organic layer was washed with 25% aqueous NH$_4$OAc, dilute NaHCO$_3$ and brine. After removal of the solvent the residue was purified by chromatography to afford the title compound. p.m.r. (CD$_3$CDCD$_3$) δ 7.1–8.2 (m, 8H), 2.55 (s, 3H).

Step 3 Preparation of 3-(2-(6-phenylpyridin-2-yl)ethenyl)benzaldehyde

A mixture of 2-methyl-6-phenylpyridine (525 mg) (step 2), isophthalaldehyde (630 mg) and dry zinc chloride (40 mg) was heated at 160° C. under N$_2$ for 3 hours. The resulting mixture was partitioned between 25% aqueous NH$_{40}$Ac (20 cc) and ethyl acetate (20 cc) The organic layer was washed with H$_2$O (10 cc), brine and solvent as removed in vacuo. The residue was purified by chromatography to afford the title compound.

p.m.r. (CD$_3$COCD$_3$) δ 10.1 (s, 1H), 7.4–8.3 (m, 14H).

Step 4 Preparation of dimethyl 5-(3-(2-(6-phenylpyridin-2-yl)ethenyl)phenyl)-4,6-dithianonanedioate To a $-5°$ C. solution of the aldehyde (step 3) (120 mg) and methyl 3-mercaptopropionate (108 mg) in dichloromethane (5 cc) was added dropwise BF$_3$.OEt$_2$ (141 mg) and the mixture was stirred for 2 hours. 25% aqueous NH$_4$OAc (20 cc) was added and the mixture was extracted with ethyl acetate (2×20 cc). The organic layer was washed with dilute NaHCO$_3$/brine and the solvents removed in vacuo. The residue was purified by chromatography to afford the title compound. p.m.r. (CD$_3$COCD$_3$) δ 7.4–8.3 (m, 14H), 5.3 (s, 1H), 3.6 (s, 6H), 2.6–3.0 (m, 8H).

Step 5

To a 0° C. solution of the diester (step 4) (140 mg) in tetrahydrofuran (1 cc) was added IM lithium hydroxide (660 μL) and the mixture was stirred for 4 hours at 25° C. The solvent was removed in vacuo and the residue taken up in H$_2$O (2 cc), acidified with acetic acid and extracted with ethyl acetate (3×5 cc). The organic layer was washed with brine and the solvents removed in vacuo to afford a residue which was purified by chromatography. The diacid obtained was treated with 2 equivalents of NaOH and freeze dried to afford the title compound. p.m.r (DMSO-d$_6$/CD$_3$COCD$_3$) δ 7.3–8.2 (m, 14H), 5.35 (s, 1H), 2.25–3.0 (m, 8H).

EXAMPLE 2

Preparation of 5-(3-(2-(5 phenylpyridin-2-yl)ethenyl)phenyl)-4,6-dithianonanedioic acid, disodium salt Step 1 Preparation of 2-methyl-5-phenylpyridine To a 0° C. solution of 1.4 M MeLi in Et$_2$O (35 mm) was added 5-phenylpyridine (4.65 g). The Et$_2$O was distilled off almost completely and replaced by THF (15 cc) and the solution was refluxed for 1 hour. 25% aqueous NH$_4$OAc (25 cc) was added and the mixture extracted with ethyl acetate (2×50 cc). The organic layer was washed with brine and the solvents removed in vacuo. The residue was purified by chromatography to afford the title compound. p.m.r. (CD$_3$COCD$_3$) δ 8.7 (d, 1H), 7.2–7.9 (m, 7H), 2.5 (s, 3H).

Step 2 Preparation of 2-bromomethyl-5-phenylpyridine

To a solution of 2-methyl-5-phenylpyridine (step 1) (169 mg) and N-bromosuccinimide (177 mg) in CCl$_4$ (3 cc) was added benzoyl peroxide (25 mg) and the mixture irradiated with visible light for 5 hours under reflux. After removal of the solvent the residue was purified by chromatography to afford the title compound.

p.m.r. (CD$_3$COCD$_3$) δ 8.8 (d, 1H), 7.4–8.1 (m, 7H), 4.7 (s, 2H).

Step 3 Preparation of ((5-phenylpyridin-2-yl)-methyl)triphenylphosphonium bromide To the bromide (step 2) (100 mg) in CH$_3$CN (2 cc) was added triphenylphosphine (400 mg) and the mixture was heated at 70° C. for 1.5 hours. The solvent was removed in vacuo and replaced by Et$_2$O (3 cc) and toluene (3 cc). The resulting solid was swished for 3 hours, filtered and dried to afford the title compound, used as such in the next step.

Step 4 Preparation of 3 (2 (5 2-yl)-ethenyl)benzaldehyde

To a −78° C. suspension of phosphonium bromide (step 3) (102 mg) in THF (3 cc) containing diisopropylamine (22 mg) is added 1.6M BuLi (131 μL) and the mixture was stirred at −78° C. for 1 hour. Isophthalaldehyde (34 mg) in THF (1 cc) was added dropwise and the reaction kept 1 hour at −78° C., then 15 minutes at 0° C. $SiO_2$ (5 cc) was added and volatiles removed in vacuo. The residue was purified by chromatography to afford the title compound. p.m.r ($CD_3COCD_3$ δ 9.1 (s, 1H), 7.9 (d, 1H), 6.4–7.2 (m, 13H).

Step 5 Preparation of dimethyl 5-(3-(2-(5-phenyl pyridin-2-yl)ethenyl)phenyl-4,6-dithianonanedioate To a 0° C. solution of aldehyde (step 4) (28 mg) and methyl 3-mercaptopropionate (30 mg) in dichloromethane (1 cc) was added $BF_3.OEt_2$ (43 mg) and the mixture was stirred for 2 hours at 0° C. 25% aqueous $NH_4OAc$ was added and the mixture extracted with ethyl acetate (2×5 cc). The organic layer was washed with brine and the solvents were removed in vacuo. The residue was purified by chromatography to afford the title compound. p.m.r. ($CD_3COCD_3$) δ 8.9 (d, 1H), 7.3–8.1 (m, 13H), 5.3 (s, 1H), 3.6 (s, 6H), 2.6–3.0 (m, 8H).

Step 6:

To the diester (step 5) (61 mg) in THF (3 cc) at 0° C. was added 1M LiOH (288 μL) and the mixture was left at room temperature for 6 hours. The THF was removed in vacuo, the residue dissolved in $H_2O$ (3 cc) and acidified with acetic acid. The mixture was extracted with ethyl acetate (2×5 cc), the organic phase washed with brine and the solvents removed to leave a residue which was purified on chromatography. The diacid obtained was treated with 2 equivalents of NaOH and freeze dried to afford the title compound.

p.m.r. ($CD_3COCD_3$) δ 8.9 (d, 1H), 7.3–8.1 (m, 13H), 5.3 (s, 1H), 2.6–3.0 (m, 8H).

What is claimed is:

1. A compound of the formula:

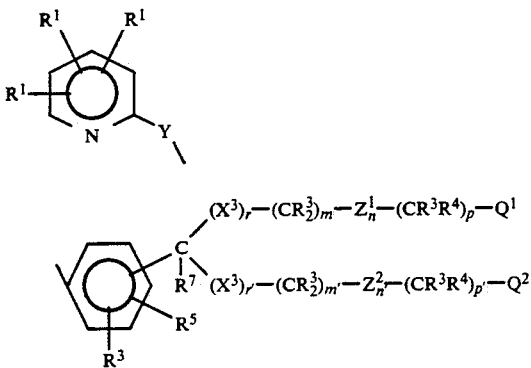

wherein:

$R^1$ is H, halogen, $C_1$–$C_8$ alkyl, $C_2$–$C_8$ alkenyl, $C_2$–$C_8$ alkynyl, —$CF_3$, —$SR^2$, —$S(O)R^2$, —$S(O)_2R^2$, —$NR^3R^3$, —$OR^3$, —$COOR^3$, —(C=O)$R^3$, —C(OH)$R^3R^3$, —CN, —$NO_2$, —$N_3$, substituted or unsubstituted phenyl, substituted or unsubstituted benzyl, substituted or unsubstituted 2-phenethyl, or substituted or unsubstituted pyridyl;

$R^2$ is $C_1$–$C_8$ alkyl, $C_2$–$C_8$ alkenyl, $C_2$–$C_8$ alkynyl, —$CF_3$, substituted or unsubstituted phenyl substituted or unsubstituted benzyl, or substituted or unsubstituted 2-phenethyl;

$R^3$ is H or $R^2$;

$R^4$ is H, halogen, —$NO_2$, —CN, —$OR^3$, —$SR^3$, $NR^3R^3$, or $C_1$–$C_8$ alkyl;

$CR^3R^4$ may be the radical of a naturally occurring amino acid selected from the group consisting of alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine;

$R^5$ is H, halogen, —$NO_2$, —$N_3$, —CN, —$SR^2$, —$NR^3R^3$, —$OR^3$, $C_1$–$C_8$ alkyl, or —(C=O)$R^3$;

$R^6$ is —$CH_2CONR^{12}R^{12}$;

$R^7$ is H or $C_1$–$C_4$ alkyl;

$R^{10}$ is —$SR^{11}$, —$OR^{12}$, or —$NR^{12}R^{12}$;

$R^{11}$ is $C_1$–$C_6$ alkyl, —(C=O)$R^{14}$, unsubstituted phenyl, or unsubstituted benzyl;

$R^{12}$ is H, $R^{11}$, or two $R^{12}$ groups joined to the same N may form pyrrolidine, piperidine, morpholine, thiamorpholine, piperazine, or N-methylpiperazine;

$R^{13}$ is $C_1$–$C_8$ alkyl, $C_2$–$C_8$ alkenyl, $C_2$–$C_8$ alkynyl, —$CF_3$, or unsubstituted phenyl, benzyl, or 2-phenethyl;

$R^{14}$ is H or $R^{13}$;

$R^{15}$ is $R^3$ or halogen;

$R^{16}$ is H, $C_1$–$C_4$ alkyl, or OH;

m and m' are independently 0–8;

n and n' are independently 0 or 1;

p and p' are independently 0–8;

m+n+p is 1–10 when $X^2$ is O, S, S(O), or $S(O)_2$;

m+n+p is 0–10 when $X^2$ is $CR^3R^{16}$;

m'+n'+p' is 1–10 when $X^3$ is O, S, S(O), or $S(O)_2$;

m'+n'+p' is 0–10 when $X^3$ is $CR^3R^{16}$;

r is 0 or 1 when $Z^1$ is HET (—$R^3$, —$R^5$);

r is 1 when $Z^1$ is —$CONR^3$;

r' is 0 or 1 when $Z^2$ is HET(—$R^3$,—$R^5$);

r' is 1 when $Z^2$ is $CONR^3$;

s is 0–3;

$Q^1$ and $Q^2$ are independently —$COOR^3$, tetrazole, —$COOR^6$, —$CONHS(O)_2R^{13}$, —CN, —$CONR^{12}R^{12}$, —CHO, —$CH_2OH$, —$COCH_2OH$, or —$NHS(O)_2R^{13}$;

$X^1$ is O, S, —S(O)—, —$S(O)_2$—, —$NR^3$, or —$CR^3R^3$—;

$X^2$ and $X^3$ are independently O, S, S(O), $S(O)_2$, or $CR^3R^{16}$;

Y is —$CR^3$=$CR^3$—, —C≡C—, —$CR^3R^3$—$X^1$—, —$X^1$—$CR^3R^3$—, —$CR^3R^3$—$X^1$—$CR^3R^3$—,

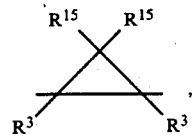

C=O,

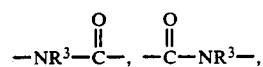

O, S, or $NR^3$;

$Z^1$ and $Z^2$ are independently —$CONR^3$—or —HET-(—$R^3$,—$R^5$)—;

HET is

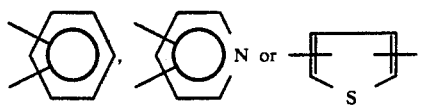

substituted phenyl, benzyl, 2-phenethyl, or pyridyl means 1 or 2 substituents on the aromatic ring selected from $C_1$-$C_6$ alkyl, $R^{10}$, $NO_2$, halogen, $-COR^7$, $-COR^{10}$, $SCF_3$, CN, and $CF_3$;

and the pharmaceutically acceptable salts thereof.

2. A compound of claim 1 of formula I' wherein the substituents are as follows:

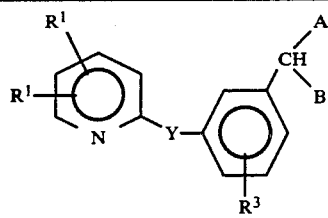

I'

| $R^1$ | $R^1$ | Y | $R^3$ | A | B |
|---|---|---|---|---|---|
| H | 5-Ph | CH=CH | H | $SCH_2CH_2CO_2H$ | $SCH_2CH_2CO_2H$ |
| H | 6-Ph | CH=CH | H | $SCH_2CH_2CO_2H$ | $SCH_2CH_2CO_2H$ |
| 6-Br | 5-Ph | CH=CH | H | $SCH_2CH_2CO_2H$ | 3-$(CO_2H)$-Phe |
| 4-$S(O)_2CH_3$ | 5-(4($SCF_3$)Phe) | $CH_2CH_2$ | 5-Ph | $SCH_2CH_2CO_2H$ | 3-$(CO_2H)$-Phe |
| H | 5-(4($C_2H_5$)Phe) | C≡C | H | $SCH_2CH_2CO_2H$ | 3-$(CO_2H)$-6-$(COCH_3)$Phe |
| 6-Ph | 3-$S(O)_2CH_3$ | CH=CH | H | $SCH_2CH_2CO_2H$ | 3-$(CO_2H)$-Phe |
| 6-Ph | H | $CH_2O$ | 4-$CH_3$ | $SCH_2CH_2CO_2H$ | 3-$(CO_2H)$-Phe |
| 5(2-$(CF_3)$Phe) | H | $CH_2O$ | H | $SCH_2CH_2CO_2H$ | 3-$(CO_2H)$-Phe |
| 6-Ph | 5-$CF_3$ | $CH_2CH_2$ | H | $SCH_2CH_2CO_2H$ | 3-$(CO_2H)$-Phe |
| 5-Cl | 6-Ph | C≡C | H | $SCH_2CH_2CO_2H$ | 3-$(CO_2H)$-Phe |
| 5-Ph | 6-$COCH_3$ | CH=CH | H | $SCH_2CH_2CO_2H$ | $CH_2CH_2$-(2($CO_2H$)Phe) |
| 6(6-Cl-2-Pyr) | H | CH=CH | H | $SCH_2CH_2CO_2H$ | $SCH_2CH_2CO_2H$ |
| 5-(4-Cl-Phe) | H | CH=CH | 6-$CF_3$ | $SCH_2CH_2CO_2H$ | $SCH_2CH_2CO_2H$. |

3. The following compounds of claim 1: 5-(3-(2-(6-phenylpyridin-2-yl)ethenyl)phenyl)-4,6-dithianonanedioic acid, disodium salt; and 5-(3-(2-(5-phenylpyridin-2-yl)ethenyl)phenyl)-4,6-dithianonanedioic acid, disodium salt.

4. A compound of claim 1 wherein:
$R^1$ is H, halogen, $C_1$-$C_8$ alkyl, $C_2$-$C_8$ alkenyl, $C_2$-$C_8$ alkynyl, $-CF_3$, $-SR^2$, $-S(O)R^2$, $-S(O)_2R^2$, $-NR^3R^3$, $-OR^3$, $-CN$, substituted or unsubstituted phenyl, substituted or unsubstituted benzyl, substituted or unsubstituted 2-phenethyl, or substituted or unsubstituted pyridyl;
$R^2$ is $C_1$-$C_8$ alkyl or $-CF_3$;
$R^4$ is H, $-OR^3$, $SR^3$, $NR^3R^3$, or $C_1$-$C_8$ alkyl;
$R^5$ is H, halogen, $-CN$, $-SR^2$, $-OR^3$, $C_1$-$C_8$ alkyl, or $-(C=O)R^3$;
$R^{13}$ is $C_1$-$C_8$ alkyl, $-CF_3$, or unsubstituted phenyl, benzyl, or 2-phenethyl;

m and m' are independently 0–4;
p and p' are independently 0–4;
m+n+p is 1–10 when $X^2$ is O or S;
m'+n'+p' is 1–10 when $X^3$ is O, or S;
$Q^1$ and $Q^2$ are independently $-COOR^3$, tetrazole, $-COOR^6$, $-CONHS(O)_sR^{13}$, $-CONR^{12}R^{12}$ or $-NHS(O)_2R^{13}$;
$X^1$ is O, S, $-NR^3$, or $-CR^3R^3-$;
$X^2$ and $X^3$ are independently O, S, or $CR^3R^{16}$;
Y is $-CR^3=CR^3-$, $-C\equiv C-$, $-CR^3R^3-X^1-$, or $-X^1-CR^3R^3-$; and the pharmaceutically acceptable salts thereof.

5. A pharmaceutical composition comprising a therapeutically effective amount of a compound of claim 1 and a pharmaceutically acceptable carrier.

6. A method of preventing the synthesis, the action, or the release of SRS-A or leukotrienes in a mammal which comprises administering to said mammal an effective amount of a compound of claim 1.

7. The method of claim 6 wherein the mammal is man.

8. A method of inducing cytoprotection in a mammal comprising administering to a mammal in need of such treatment a cytoprotective amount of a compound of claim 1.

9. A method of treating inflammatory diseases of the eye in a mammal which comprises administering to a mammal in need of such treatment a therapeutically effective amount of a compound of claim 1.

10. The method of claim 9 wherein the mammal is man.

* * * * *